United States Patent
Lillegard et al.

(10) Patent No.: US 9,603,540 B2
(45) Date of Patent: Mar. 28, 2017

(54) ELECTRODE PLACEMENT FOR REMOTE MONITORING

(75) Inventors: Gregory A. Lillegard, Menonomee Falls, WI (US); Cameron Brackett, Pewaukee, WI (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1172 days.

(21) Appl. No.: 12/357,063

(22) Filed: Jan. 21, 2009

(65) Prior Publication Data
US 2010/0185114 A1    Jul. 22, 2010

(51) Int. Cl.
- A61B 5/00     (2006.01)
- A61B 5/0402   (2006.01)
- A61B 5/0408   (2006.01)
- A61B 5/06     (2006.01)

(52) U.S. Cl.
CPC ........ *A61B 5/0402* (2013.01); *A61B 5/04085* (2013.01); *A61B 5/061* (2013.01)

(58) Field of Classification Search
CPC . A61B 5/0402; A61B 5/0408; A61B 5/04087; A61B 5/0448; A61B 5/04012; A61B 5/0488; A61B 5/0006; A61B 5/061

USPC .......... 600/546, 544, 484, 483, 301; 607/46
See application file for complete search history.

(56) References Cited

U.S. PATENT DOCUMENTS

| | | | |
|---|---|---|---|
| 5,137,458 A * | 8/1992 | Ungs et al. | 434/262 |
| 6,178,357 B1 * | 1/2001 | Gliner et al. | 607/142 |
| 7,511,623 B2 | 3/2009 | Tice | |
| 7,668,588 B2 * | 2/2010 | Kovacs | 600/509 |
| 2006/0167367 A1 * | 7/2006 | Stanczak et al. | 600/523 |
| 2006/0247504 A1 | 11/2006 | Tice | |
| 2007/0024439 A1 | 2/2007 | Tice | |
| 2007/0083089 A1 | 4/2007 | Tice | |
| 2007/0232946 A1 * | 10/2007 | Feild et al. | 600/509 |
| 2008/0039904 A1 * | 2/2008 | Bulkes et al. | 607/62 |

FOREIGN PATENT DOCUMENTS

JP    2005230540    * 9/2005

* cited by examiner

*Primary Examiner* — Max Hindenburg
(74) *Attorney, Agent, or Firm* — Husch Blackwell LLP

(57) ABSTRACT

A method of placing ECG electrodes in an environment where persons of limited training are available includes making a trial placement of the electrodes. Then, the method includes testing the electrodes and evaluating signals from the electrodes as a result of the testing. Verbal or visual feedback can be provided to the person placing the electrodes so that placed electrodes could be adjusted as needed.

19 Claims, 3 Drawing Sheets

ELECTRODE PLACEMENT FOR REMOTE MONITORING

FIELD

The invention pertains to monitoring of physiological conditions of individuals. More particularly, the invention pertains to remote monitoring of such individuals.

BACKGROUND

Various types of monitoring systems of physiological conditions of an individual are known. Some of these monitoring systems are intended to be used by individuals in their residences on an on-going daily basis to implement home based disease management programs.

Representative monitoring systems are disclosed in the application titled "In-Residence Monitoring System Incorporating Voice Output", assigned U.S. Ser. No. 11/226,550, and filed Sep. 14, 2005; the application titled "Monitoring System for a Residence", assigned U.S. Ser. No. 11/189,332, and filed Jul. 26, 2005; and the application titled "Residential Monitoring System for Selected Parameters", assigned U.S. Ser. No. 11/119,182, and filed Apr. 29, 2005 all of which are assigned to the Assignee hereof and incorporated herein by reference. Such systems are often intended to be used in an environment where they communicate, usually intermittently, with a displaced monitoring facility staffed by trained health care professionals who are able to evaluate the results being received from a monitoring unit local to the resident or patient.

An electrocardiogram (ECG) is recognized as a non-invasive relatively simply way to diagnose heart conditions. Twelve lead or electrode electrocardiograms are commonly used for diagnosis by trained medical personnel in clinical settings. In such settings, the person conducting the evaluation knows where to place the electrodes on the individual being evaluated.

Electrocardiograms have also been recognized as valuable cardiac evaluation tools for remotely monitored patients. However, in these settings, the person who is having the test or a caregiver of limited training will probably be the only ones available to place the electrodes.

Currently in such settings, ECGs are limited to 2 electrodes providing a single lead ECG because anything beyond two electrodes becomes too difficult for most patients or their caregivers to apply. Unfortunately, the single lead ECG provides little clinical value beyond heart rate.

Color coded electrodes are known and used in monitoring patients. Methods for detecting potentially bad electrode placements are also known and in use.

There is a continuing need to make it possible for residents or patients who may be living in their homes with or without caregivers with limited training and who are being remotely monitored to more effectively make ECG electrode placements.

DETAILED DESCRIPTION

Figure 1A:
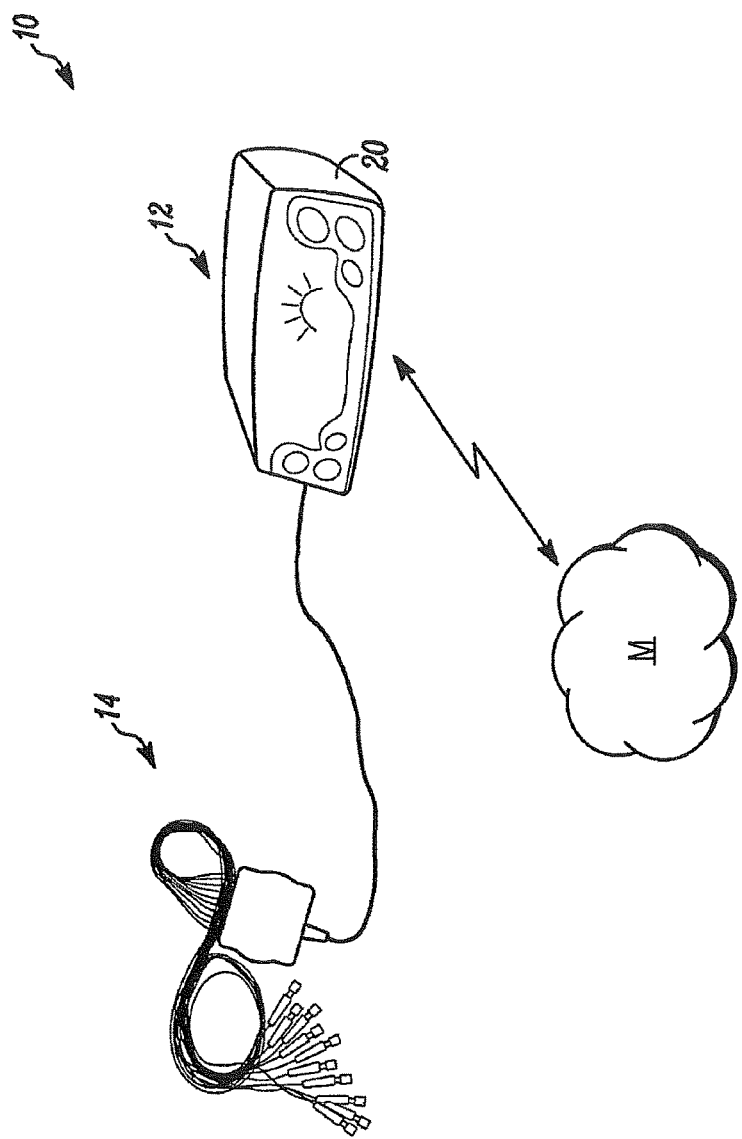
FIG. 1A is a diagram illustrating aspects of an embodiment of the invention.
Figure 1A:
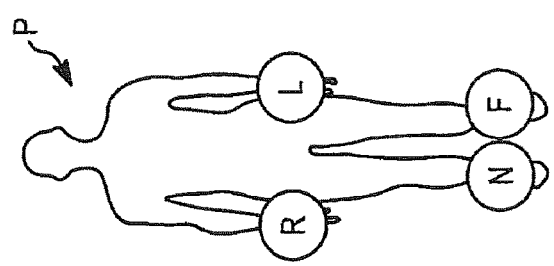

While embodiments of this invention can take many different forms, specific embodiments thereof are shown in the drawings and will be described herein in detail with the understanding that the present disclosure is to be considered as an exemplification of the principles of the invention as well as the best mode of practicing the same and is not intended to limit the invention to the specific embodiment illustrated.

In embodiments of the invention, combining color coded ECG electrodes (more pronounced size and color), electrode placement evaluation to detect improper electrode placement, and voice guidance provides a higher level of proper successful electrode placement and attachment by untrained patients. If an electrode appears to have been placed incorrectly, then voice feedback locally generated or from a remote monitoring site can be provided to instruct the patient as to which electrode is improperly placed and how to move it to a better location.

In one aspect of the invention, the patient is instructed as to correct electrode placement. After placing electrodes the patient requests a test of the electrode placement. During the test, the signal from the electrodes is analyzed in real time to look for likely problems. Common issues (poor contact, reversed electrodes, etc.) are detected by the processing, and additional voice feedback can be used to instruct the patient on what correct action to take. After the patient attempts to correct the problem the electrode placement is retested prior to making a diagnostic evaluation.

Figure 1B:
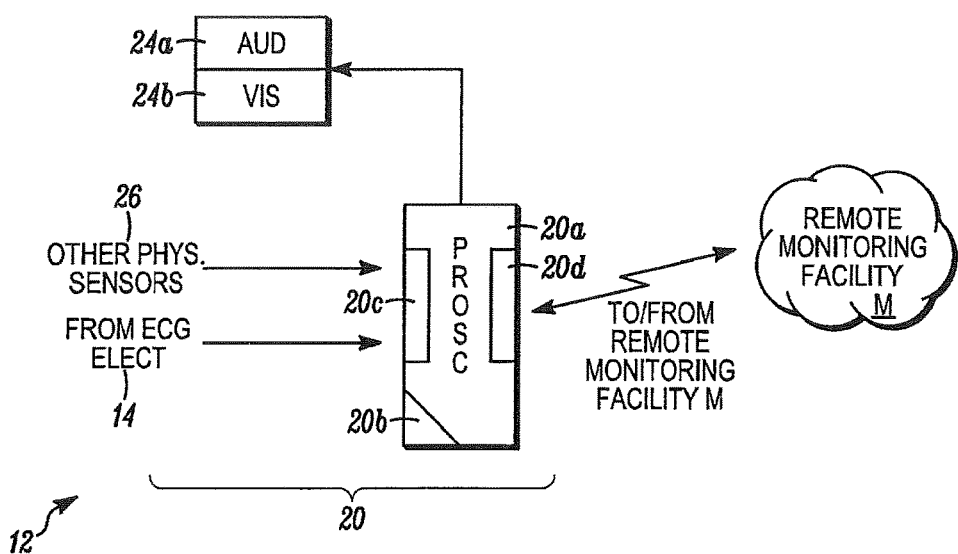
FIG. 1B is a diagram that illustrates additional aspects of the embodiment of FIG. 1A.

FIGS. 1A and 1B illustrate details of an apparatus 10 that embodies the present invention. The apparatus 10 includes a monitoring unit 12 that might be situated proximate to a resident or patient P, for example, in the resident's house, living room, bedroom, or the like. The unit 12 can receive inputs from a plurality of color coded ECG electrodes 14 each of which is intended to be place on or coupled to the resident at a predetermined location indicated in FIG. 1A as, R, L, N, and F. Placement is important in obtaining a diagnostically useful set of signals at the unit 12.

In accordance with the invention, the individual P can place the electrodes on himself or herself as best as possible. The ECG test can then be started at the unit 12. Current from the electrodes 14 detected by the unit 12 can be processed locally or at a remote monitoring facility M to evaluate placement of the electrodes 14. For example, if the R and L electrodes are switched, then an absence of expected types of signals, such as Q or R amplitude from the appropriate electrode, can be detected. The unit 12 can then automatically generate a verbal output to the individual P that the two electrodes need to be switched.

The individual P, after switching the electrodes and placing them into locations that are as appropriate as possible, can rerun the test. If appropriate signals are detected at the unit 12, then these can then be analyzed locally, or digital representations thereof can be transmitted to the remote monitoring facility M for analysis.

Those of skill will understand that numerous other types of electrode placement errors can be sensed at the unit 12 or at the facility M, and automatic verbal outputs can then be generated at the unit 12 to advise the person P as to how the placement should be adjusted to correct the detected problem.

In accordance with the above, the unit 12 can be carried in a housing 20 as seen FIGS. 1A and 1B. The unit 12 can include control circuitry that could be implemented at least in part with a programmable processor 20a and associated control software 20*b*. The software 20*b* can be stored in executable form in read-only memory, programmable read-only memory, or any other desired medium at the control circuitry.

The software 20*b* could carry out local signal analysis to evaluate incoming signals from the electrodes 14 as well as generate and control verbal and/or visual outputs via local output units, such as a speaker 24*a* and a display unit 24*b*.

The control software 20*b* could carry out other monitoring related functions as would be understood by those of skill in the art. For example, the software 20*b* can present on the visual display 24*b* a graphical, educational display as to how the electrodes should be placed and how they should be rearranged to address a problem or problems detected by the analysis software 20*b*.

Signals from the ECG electrodes 14 and other types of physiological sensors 26, such as blood pressure sensors, temperature sensors, and the like, all without limitation, can be coupled to the control circuitry via interface circuits 20*c*. The control circuitry can also communicate bi-directionally via an interface 20*d* wired or wirelessly with the remote monitoring facility M.

Figure 2:
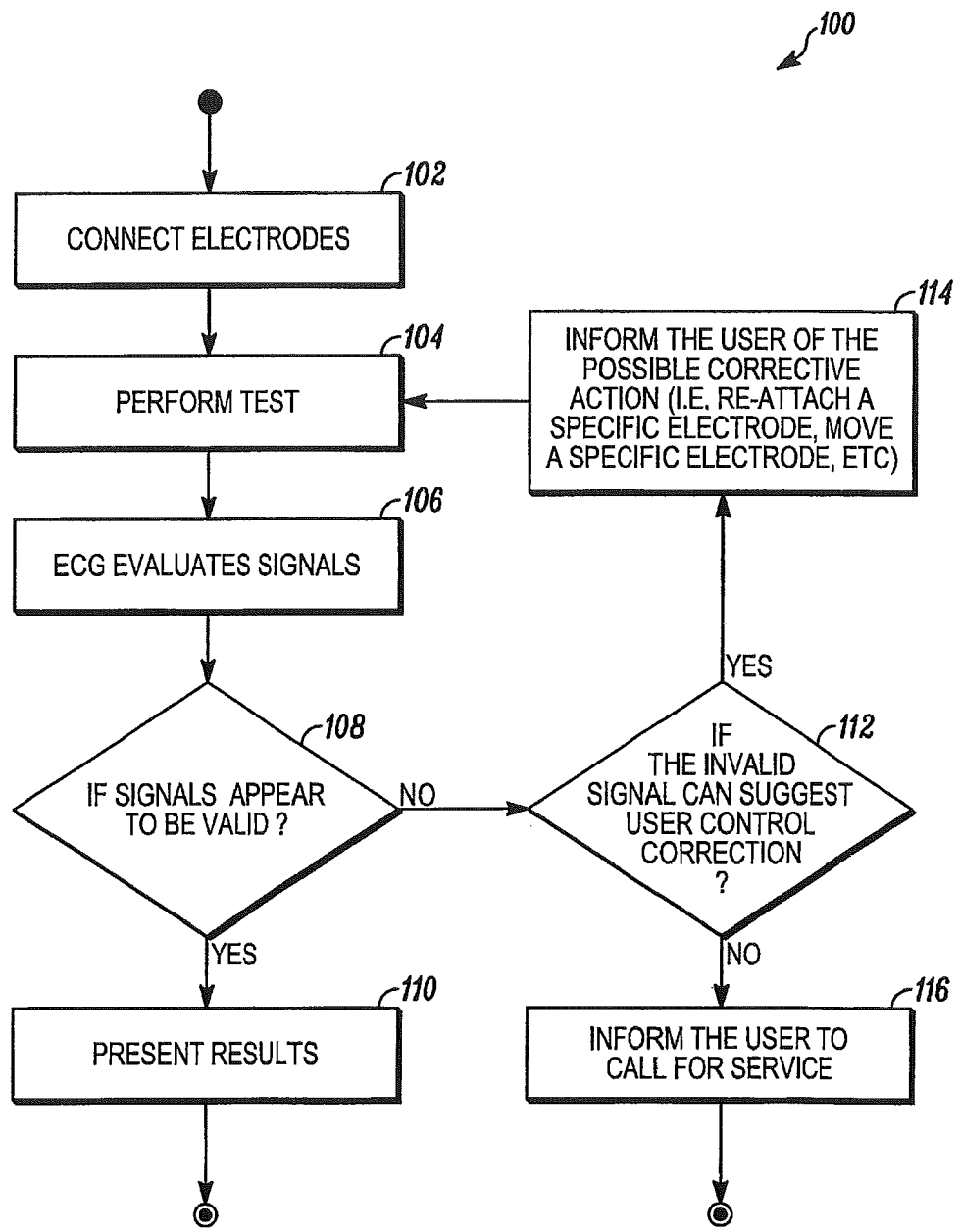
FIG. 2 is a flow diagram illustrating aspects of a method in accordance with the invention.

FIG. 2 illustrates a method 100 that embodies the invention. Initially, the individual P places the electrodes on himself, herself, or a person that is being tested, as at 102. The unit 12 is activated to perform an ECG, as at 104.

The unit 12 evaluates signals received from the electrodes 14 or transfers representations of those signals to the facility M for analysis, as at 106. A determination is made, as at 108, as to validity of the received signals. If the signals are acceptable, then results can be presented locally, both verbally or audibly and visually via the speaker 24*a* and the graphical display device 24*b*, as at 110. Alternately or additionally, such results can be transmitted to the facility M and reviewed or stored in the chart of the individual P.

When analysis of signals from the electrodes 14 reveals a problem with electrode placement, the unit 12 can provide verbal or visual correctional feedback, as at 112, via the speaker 24*a* and the display device 24*b* to the person P or to that person's caregiver as to how the placement of the electrodes could be adjusted to provide better results, as at 114. If the analysis indicates that there is an uncorrectable problem, then verbal or visual feedback can be provided to the user, as at 116, that service needs to be called.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A method of placing electrodes comprising:
   prior to placement of the electrodes of a monitoring unit on an individual person, providing instructions as to correct placement of the electrodes;
   placing the electrodes at various locations on the individual person;
   control circuitry of the monitoring unit determining when current sent from the individual person through the electrodes is indicative of the electrodes being reversed and that the electrodes can be corrected by a user;
   when the current sent from the individual person through the electrodes is indicative of the electrodes being reversed and that the electrodes can be corrected by the user, the control circuitry evaluating the placement of the electrodes based on the current sent from the individual person through the electrodes, and the control circuitry providing verbal feedback relative to the placement of the electrodes on the individual person, the verbal feedback including instructions that two of the electrodes need to be switched; and
   when the current sent from the individual person through the electrodes is not indicative of the electrodes being reverses and that the electrodes can be corrected by the user, the control circuitry providing feedback for the user to call for service.

2. A method as in claim 1 further comprising testing the electrodes prior to the evaluating.

3. A method as in claim 2 further comprising transmitting signals from the electrodes to a remote location.

4. A method as in claim 3 wherein the evaluating includes comparing the signals to a predetermined standard.

5. A method as in claim 4 further comprising providing the verbal feedback responsive to the comparing.

6. A method as in claim 5 further comprising providing visual feedback relative to the placement of the electrodes.

7. A method as in claim 6 wherein the instructions include a visual display as to how the electrodes should be placed.

8. A method of placing electrodes comprising:
   prior to placement of the electrodes on an individual person, providing instructions as to correct placement of the electrodes;
   making a trial placement of the electrodes on the individual person;
   control circuitry testing performance of the electrodes placed on the individual person;
   the control circuitry determining when signals from the individual person through the electrodes are indicative of the electrodes being reversed and that the electrodes can be corrected by a user;
   when the signals from the individual person through the electrodes are indicative of the electrodes being reversed and that the electrodes can be corrected by the user, the control circuitry evaluating the signals from the individual person through the electrodes as a result of the testing, and the control circuitry providing verbal feedback from a remote location to the user, the verbal feedback including instructions that two of the electrodes need to be switched; and
   when the signals from the individual person through the electrodes are not indicative of the electrodes being reversed and that the electrodes can be corrected by the user, the control circuitry providing feedback for the user to call for service.

9. A method as in claim 8 further comprising automatically providing the verbal feedback.

10. A method of placing electrodes comprising:
    prior to placement of the electrodes of a monitoring unit on an individual person, providing instructions as to correct placement of the electrodes;
    placing the electrodes at a plurality of locations on the individual person;
    control circuitry of the monitoring unit determining when current sent from the electrodes is indicative of the electrodes being reversed and that the electrodes can be corrected by a user;
    when the current sent from the electrodes is indicative of the electrodes being reversed and that the electrodes can be corrected by the user, the control circuitry automatically testing performance of the electrodes and obtaining position indicating signals therefrom, and the control circuitry evaluating the position indicating signals from the electrodes and, responsive thereto, providing verbal feedback as to the placement of the electrodes on the individual person, the verbal feedback including instructions that two of the electrodes need to be switched; and when the current sent from the electrodes is not indicative of the electrodes being reversed and that can the electrodes be corrected by the user, the control circuitry providing feedback for the user to call for service.

11. A method as in claim 10 wherein the instructions explain how to move at least one of the electrodes to improve the position indicating signals.

12. A method as in claim 10 further comprising retesting the performance of the electrodes subsequent to at least one of the electrodes having been moved.

13. A method as in claim 12 further comprising providing test results at a displaced location.

14. A method as in claim 10 further comprising automatically providing the verbal feedback.

15. A method as in claim 14 further comprising retesting the performance of the electrodes subsequent to at least one of the electrodes having been moved.

16. An apparatus for placing a plurality of person monitoring electrodes comprising:

control circuits that are coupled to the plurality of person monitoring electrodes; and an audio output device that is coupled to the control circuits, wherein the control circuits generate instructions as to correct placement of the plurality of person monitoring electrodes prior to placement of any of the plurality of person monitoring electrodes on an individual person, evaluate at least one signal received from the individual person through the plurality of person monitoring electrodes placed on the individual person, and responsive thereto, determine when the at least one signal is indicative of the electrodes being reversed and that the electrodes can be corrected by a user, wherein, when the at least one signal is indicative of the electrodes being reversed and that the electrodes can be corrected by the user, the control circuits automatically generate a verbal message indicative of the placement of the plurality of person monitoring electrodes on the individual person, the verbal message including instructions that two of the plurality of person monitoring electrodes need to be switched, and wherein, when the at least one signal is not indicative of the electrodes being reversed and that the electrodes can be corrected by the user, the control circuits provide feedback for the user to call for service.

17. An apparatus as in claim 16 wherein the control circuits include executable software pre-recorded on a computer readable medium, which, at least in part, carries out an evaluation of the at least one signal.

18. An apparatus as in claim 17 wherein the control circuits evaluate at least one other signal received from the individual person through the plurality of person monitoring electrodes, and responsive thereto, automatically generate another verbal message indicative of the placement of the plurality of the person monitoring electrodes.

19. An apparatus as in claim 18 where indicia the at least one signal or the at least one other signal is transmitted to a displaced facility.

* * * * *